(12) United States Patent
Perez

(10) Patent No.: US 8,282,803 B2
(45) Date of Patent: Oct. 9, 2012

(54) ISOELECTRIC FOCUSING TRAY AND ELECTRODE ASSEMBLY FOR ALTERNATE GEL STRIP ORIENTATIONS

(75) Inventor: Evelio Perez, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 226 days.

(21) Appl. No.: 12/730,600

(22) Filed: Mar. 24, 2010

(65) Prior Publication Data

US 2010/0243452 A1    Sep. 30, 2010

Related U.S. Application Data

(60) Provisional application No. 61/163,289, filed on Mar. 25, 2009.

(51) Int. Cl.
*B01D 57/02* (2006.01)
(52) U.S. Cl. .......................... 204/610; 204/459; 204/644
(58) Field of Classification Search ................... 204/601, 204/600, 459, 450, 610
See application file for complete search history.

(56) References Cited

U.S. PATENT DOCUMENTS

| | | | |
|---|---|---|---|
| 4,552,640 | A  | 11/1985 | Kartenbeck |
| 6,932,895 | B2 | 8/2005  | Anderson et al. |
| 2003/0141190 | A1 | 7/2003 | Alpenfels et al. |
| 2004/0079638 | A1 | 4/2004 | Rooney et al. |
| 2005/0072678 | A1 | 4/2005 | Hunter et al. |

*Primary Examiner* — Alex Noguerola
*Assistant Examiner* — Gurpreet Kaur
(74) *Attorney, Agent, or Firm* — Kilpatrick Townsend & Stockton LLP.; M. Henry Heines

(57) ABSTRACT

The procedures involved in isoelectric focusing that entail the use of an electric current can be performed with the gel side of the IPG strip facing either up or down in a tray and electrode assembly in which the electrodes are mounted on an insert from which the inner ends of the electrodes extend into the troughs to reside either below the IPG strips or above them. Slots in one part (either the insert or the tray) mate with walls or partitions in the other part to secure the two parts together, and the heights of the electrodes within the troughs of the tray can be adjusted by the height of the insert in the tray or by a resilient mounting of the electrode to the insert.

25 Claims, 7 Drawing Sheets

ISOELECTRIC FOCUSING TRAY AND ELECTRODE ASSEMBLY FOR ALTERNATE GEL STRIP ORIENTATIONS

CROSS-REFERENCE TO RELATED APPLICATION

This application claims the benefit of U.S. Provisional Patent Application No. 61/163,289, filed Mar. 25, 2009, the contents of which are incorporated herein by reference.

BACKGROUND OF THE INVENTION

1. Field of the Invention

This invention resides in the field of laboratory equipment for electrophoretic separations, and the particular equipment addressed herein is that designed for isoelectric focusing.

2. Background of the Invention

As is well known in the art, isoelectric focusing is the separation of proteins into a linear array according to their isoelectric points and is performed on a sample for purposes of detection, analysis, and in some cases quantification of the proteins in the sample. Isoelectric focusing is typically performed in gel strips that contain immobilized pH gradients ("IPG strips"), and can serve either as the entire separation process of the proteins, or as the first dimension of a two-dimensional separation. In two-dimensional separations, the second dimension is performed by placing the IPG strip, after the first dimension separation has been performed, along one edge of a two-dimensional ("slab"-shaped) separation medium and imposing an electric field on the two-dimensional medium in a direction transverse to the IPG strip. This causes the proteins in each focused zone in the IPG strip to migrate into, and spread out within, the slab, thereby extending the linear array in the IPG strip to a two-dimensional array. The proteins in the original sample thus have the benefit of being separated according to two parameters. Descriptions of isoelectric focusing and some of the equipment in which isoelectric focusing is performed can be found in Panattoni, "Assembly for Casting and Use of an Isoelectric Focusing Strip," U.S. Pat. No. 6,655,649, issue date Dec. 2, 2003; Williams et al., "Apparatus for Electrophoresis," U.S. Pat. No. 6,558,522, issue date May 6, 2003; Faupel et al., "Isoelectric Focusing Apparatus," U.S. Pat. No. 5,082,548, issue date Jan. 21, 1992; and Witkorowicz et al., "Electrophoresis Apparatus and Method," U.S. Pat. No. 6,214,191, issue date Apr. 10, 2001.

IPG strips are commercially available from suppliers to biochemical laboratory suppliers and are commonly supplied in dehydrated form to be rehydrated by the user prior to use in the separation procedure. Both rehydration and focusing are typically performed in trays that accommodate as many as 24 IPG strips for simultaneous separations of as many samples. In some procedures, rehydration is performed in a rehydration/equilibration tray and once rehydrated, the strips are transferred to a separate focusing tray. In other procedures, rehydration and focusing are performed in the same tray. When the same tray, or any tray with electrodes contacting the strips, is used, rehydration can be performed in the presence of an electric current ("active rehydration"). This is particularly useful when the sample is combined with the rehydration solution and contains high molecular weight proteins, since the current enhances the entry of the proteins into the IPG strip. In certain separations, the sample is loaded through a separate receptacle at one end of the IPG strip, i.e., by "cup loading," while in others the sample is applied to the entire length of the strip.

The typical IPG strip obtained from a supplier is a thin, flat strip of gel material that has a backing on one side for dimensional stability and ease of handling and a protective sheet on the other side. The protective sheet is removed by the user prior to rehydration and discarded, while the backing remains in place throughout both the rehydration and focusing. The strip thus contains a "gel side" and a backing side, and with the gel in a horizontal position the gel side can be facing either up or down during the rehydration step, and either up or down during the focusing step, depending on the needs of the sample to be separated, the preference of the user, or both. During focusing and active rehydration, however, the electrodes must be in contact with the gel side. The trays presently available are designed for use with gels in either one orientation or the other, i.e., trays intended for contact of the electrodes with gels whose gel sides are facing up are distinct in their design and construction from trays intended for contact of the electrodes with gel sides facing down.

SUMMARY OF THE INVENTION

The present invention resides in apparatus in which active rehydration, isoelectric focusing, or both can be performed either with the gel side of the IPG strip facing up and the electrode thus above the strip, or with the gel side facing down and the electrode thus beneath the strip, and with gels of a range of thicknesses in either orientation. This variability is achieved by constructing the tray and electrodes as separate components, i.e., placing the electrodes in a removable insert, or preferably two such inserts, one for each end of the tray. The electrodes in each insert terminate at their inner ends in exposed extensions, such as tabs or bars, that are either of metal or of a support material such as plastic with metal wires or strips on both their upper and lower surfaces. The tray contains a series of parallel channels or troughs, each sized to receive one IPG strip. The electrodes are mounted to the insert such that when the insert is in place in the tray, the exposed inner ends of the electrodes are inside the troughs, either in direct contact with, or close to, the floors of the troughs, with electrode material being exposed on both sides of each electrode end for contact with a gel either above or below the electrode. Each exposed inner end of an electrode is sufficiently narrow to fit within one trough of the tray, and in preferred constructions, each insert contains slots between the electrode tabs to engage partitions that separate the troughs. The height of the exposed inner end of each electrode relative to the floor of each trough is manually adjusted in certain embodiments of the invention by user control of how far the insert is pushed into the tray. In other embodiments, the height of the exposed inner end of each electrode is automatically set by a spring-loaded or otherwise resilient mounting of the electrode, urging the exposed inner end toward the trough floor. With resiliently mounted electrodes, therefore, the height of each exposed inner end within its corresponding trough depends on whether a gel has been placed in the trough before or after the insert, and if before, on the thickness of the gel. Thus, when rehydration, isoelectric focusing, or both are to be performed with gel sides down, the insert is placed in the tray before the gels, and is inserted far enough that the inner electrode ends contact the floor of each empty trough. When the procedure is to be performed with gel sides up, the gels are placed in the troughs before the inserts, and the inserts are placed above the gels.

Among the advantages of this invention are the user's ability to use a single apparatus for active rehydration and isoelectric focusing in either orientation of the IPG strip, and to choose between loading the sample either by cup loading or by applying the sample to the entire IPG strip. Further advantages are the ability of the apparatus to accommodate IPG strips of both orientations at the same time by placing one or more strips in troughs of the tray before the insert is lowered into position and one or more other strips in other troughs of the same tray after the insert is lowered into position, and the ability of the apparatus to accommodate IPG strips of different thicknesses in a single tray.

These and other features, embodiments, and advantages of the invention will be apparent from the description that follows.

BRIEF DESCRIPTION OF THE DRAWINGS

FIG. 1a is a perspective view of one example of a tray and insert assembly in accordance with the present invention.

FIG. 1b is a top view of the assembly of FIG. 1a.

FIG. 1c is a cross section of the assembly of FIGS. 1a and 1b taken along the line C-C of FIG. 1b.

DETAILED DESCRIPTION OF THE INVENTION AND PREFERRED EMBODIMENTS

Figure 1:
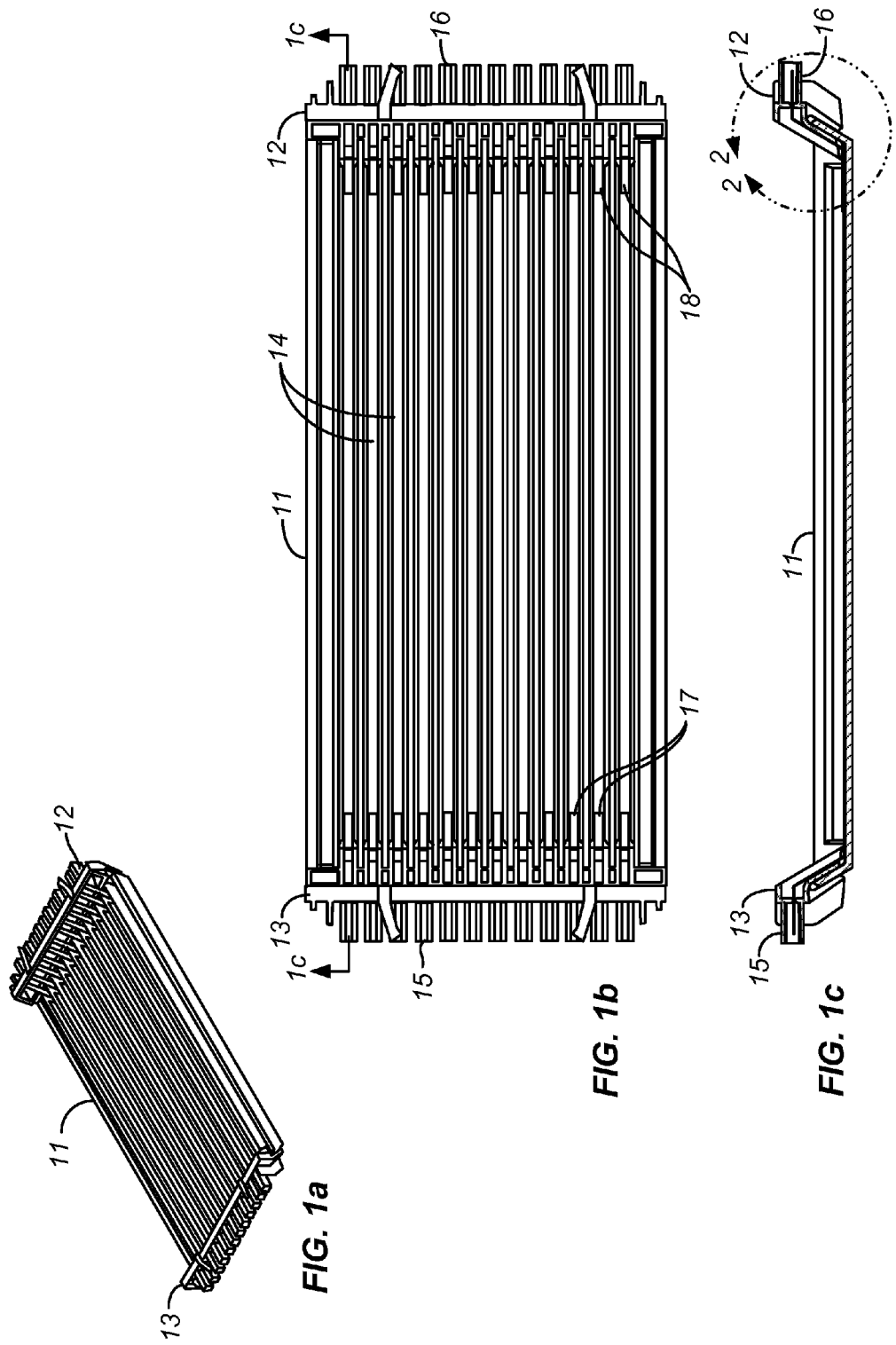

While the features defining this invention are capable of implementation in a variety of constructions, the invention as a whole will be best understood by a detailed examination of specific embodiments. Two such embodiments are shown in the drawings.

The first embodiment is illustrated in a perspective view in FIG. 1a, a top view in FIG. 1b, and a vertical cross section in FIG. 1c. The cross section in FIG. 1c is taken along the line C-C in FIG. 1b. The tray 11 in these Figures is shown with an insert 12 at one end and a second insert 13 at the opposite end. The tray 11 contains twelve troughs 14, which are elongate and parallel and sized to accommodate one IPG strip each. Each insert extends the full width of the tray, spanning all troughs. Each insert 12, 13 contains a set of plugs 15, 16 for external electrical connections, one plug for each of the twelve troughs, and a set of electrodes, one for each of the twelve troughs, to contact the gels. The flat inner ends 17, 18 of the electrodes are either metal tabs or plastic tabs with metal wires or strips fixed to both surfaces of the tabs, and serve as the contact electrodes for the gel strips.

Figure 2:
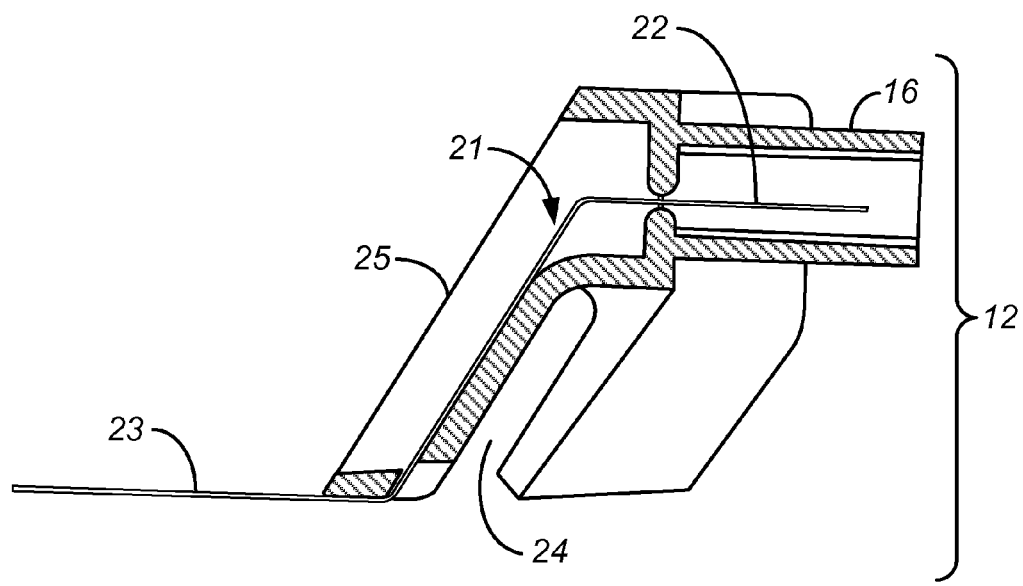
FIG. 2 is a cross section of the insert of FIGS. 1a, 1b, and 1c.
Figure 3:
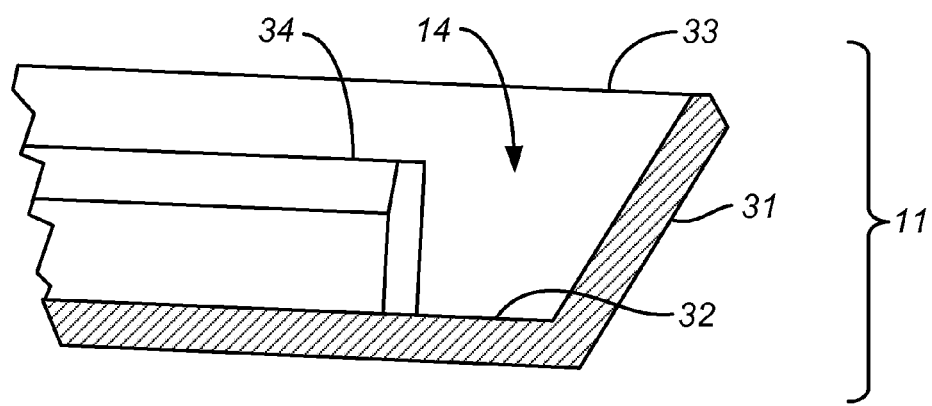
FIG. 3 is a cross section of one end of the tray of FIGS. 1a, 1b, and 1c.
Figure 4:
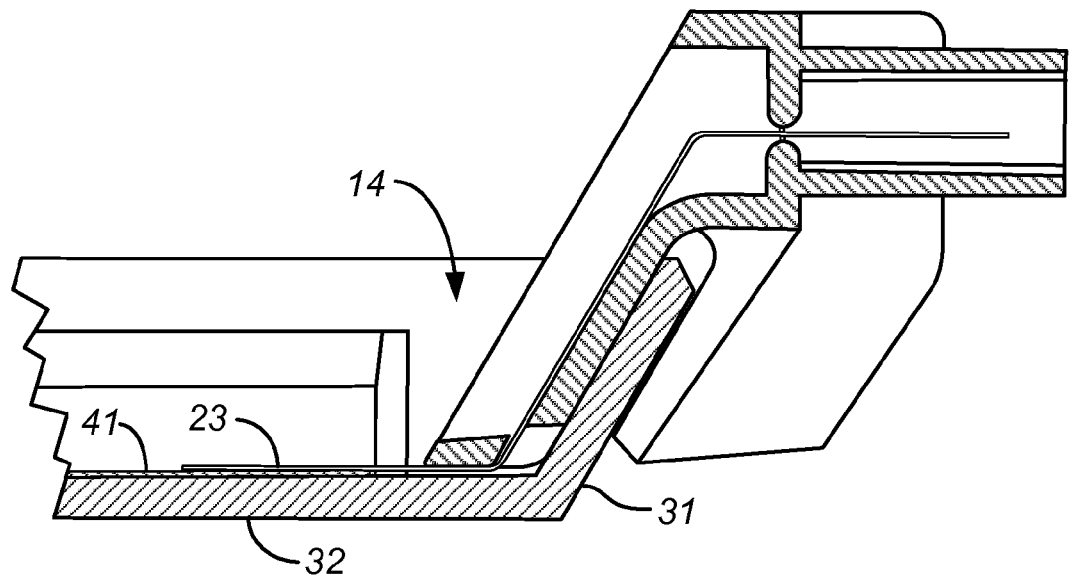
FIG. 4 is a cross section of the assembled insert and tray of FIGS. 2 and 3 arranged to accommodate a gel beneath the electrode.
Figure 5:
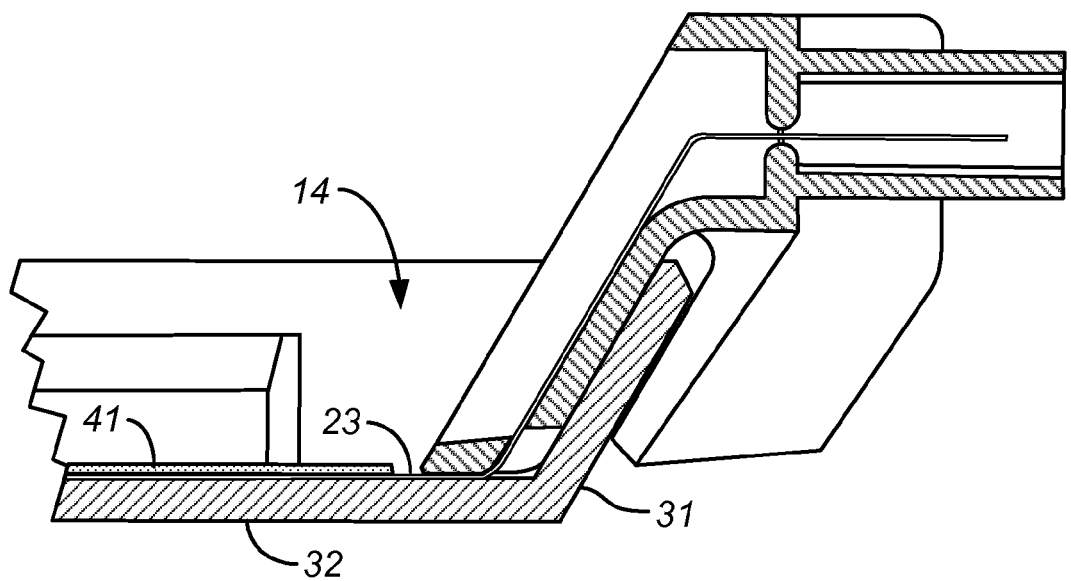
FIG. 5 is a cross section of the assembled insert and tray of FIGS. 2 and 3 arranged to accommodate a gel above the electrode.

An enlarged view of one of the inserts is shown in FIG. 2, an enlarged view of the end of the tray where the insert is inserted is shown in FIG. 3, and enlarged views of the insert and tray together are in FIGS. 4 and 5. These views correspond to the portion of FIG. 1c indicated by the dashed circle 2 and are all cross sections taken along the same plane as that of FIG. 1c.

In the cross section of the insert 12 in FIG. 2, the electrode 21 extends from an outer end 22 inside the plug 16 to its inner end 23, which in this case is a narrow flat metal tab with exposed upper and lower surfaces. A single transverse slot 24 in the insert (i.e., transverse to the lengthwise direction of the trough and of the electrode 21) fits over the transverse end wall (shown in FIG. 3 and discussed below) of the tray. Adjacent electrodes are separated by barriers, one of which 25 is visible in FIG. 2. Each barrier has a longitudinal slot (not visible in FIG. 2) that fits over the partitions in the tray that divide the tray into troughs.

The tray 11 is shown in cross section in FIG. 3. The Figure shows the interior of a single trough 14 of the tray, terminating at its end in the transverse end wall 31, which is received within the transverse slot 24 of the insert. The trough is closed at the bottom by a floor 32, and adjacent troughs are separated by partitions 33 (referred to in the preceding paragraph) of which one is shown. A reinforcing structure 34 is molded onto the inner surface of the partition 33.

FIGS. 4 and 5 show the assembled tray and insert with an IPG strip 41. In FIG. 4, the IPG strip 41 has been placed on the floor of the trough 14 before the insert has been placed in position. The inner end 23 of the electrode therefore lies above the IPG strip, contacting the upper side of the strip, and the IPG strip 41 has been placed with the gel side up to contact the electrode. In FIG. 5, the insert has been placed in the tray before the IPG strip 41, and the IPG strip has been placed over the electrode with the gel side down. The inner end 23 of the electrode thus lies below the IPG strip and the gel side of the IPG strip again contacts the electrode. The insert resides slightly lower in the tray in the FIG. 5 position than in the FIG. 4 position. The tray and insert combination can thus accommodate gels of any thickness and can be used with the electrode contacting either the top of the gel or the bottom of the gel.

Figure 6:
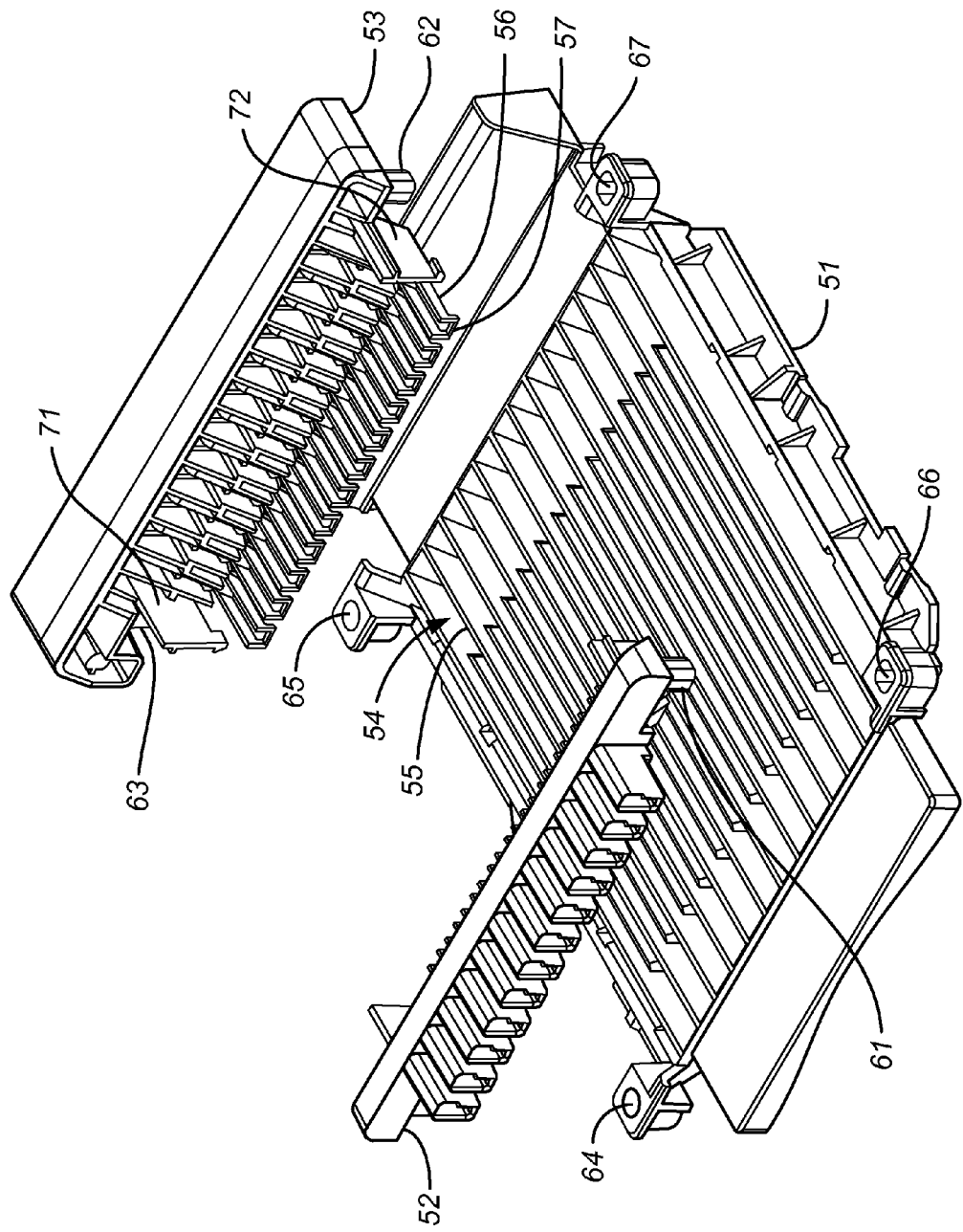
FIG. 6 is a perspective view of a second example of a tray and insert assembly in accordance with the present invention.

The second embodiment is illustrated in the succeeding Figures. FIG. 6 is a perspective view of the tray 51 and two inserts 52, 53 raised above the tray for visibility. Like the tray 11 of the embodiment of FIG. 1, the tray 51 in the embodiment of FIG. 6 has twelve troughs 54, separated by partitions 55, and each insert has twelve electrodes 56 of which only those on the right insert are visible. A feature that distinguishes the inserts in this embodiment from those of the embodiment of FIGS. 1-5 is the configurations of the inner ends of the electrodes 56. In the embodiment of FIG. 6, each individual electrode is a loop at its inner end, terminating in a right-angle downward bed and a crossbar 57. The gel strip fits between the two longitudinal side arms of the loop. The crossbar 57 spans the width of the gel and serves as the electrical contact with the gel, either above or below the gel. Further views of the loop and crossbar appear in FIGS. 7 and 8, discussed below.

Another feature that distinguishes the inserts in this embodiment from those of the embodiment of FIGS. 1-5 is the inclusion of positioning posts on the inserts and complementary holes in the tray to receive the posts. Only the posts 61, 62 on one end of each of the inserts are fully visible in this perspective view, while further posts, one of which 63 is partially visible, are similarly situated on the opposite ends of the inserts. All four holes 64, 65, 66, 67 in the tray are visible, one hole in direct alignment with each of the four posts. To ensure proper placement of the inserts in the tray, one post on each insert has a square cross section (with rounded corners)

while the other has a circular cross section, the corresponding holes having complementary cross sections to allow insertion of only the proper post.

Figure 10:
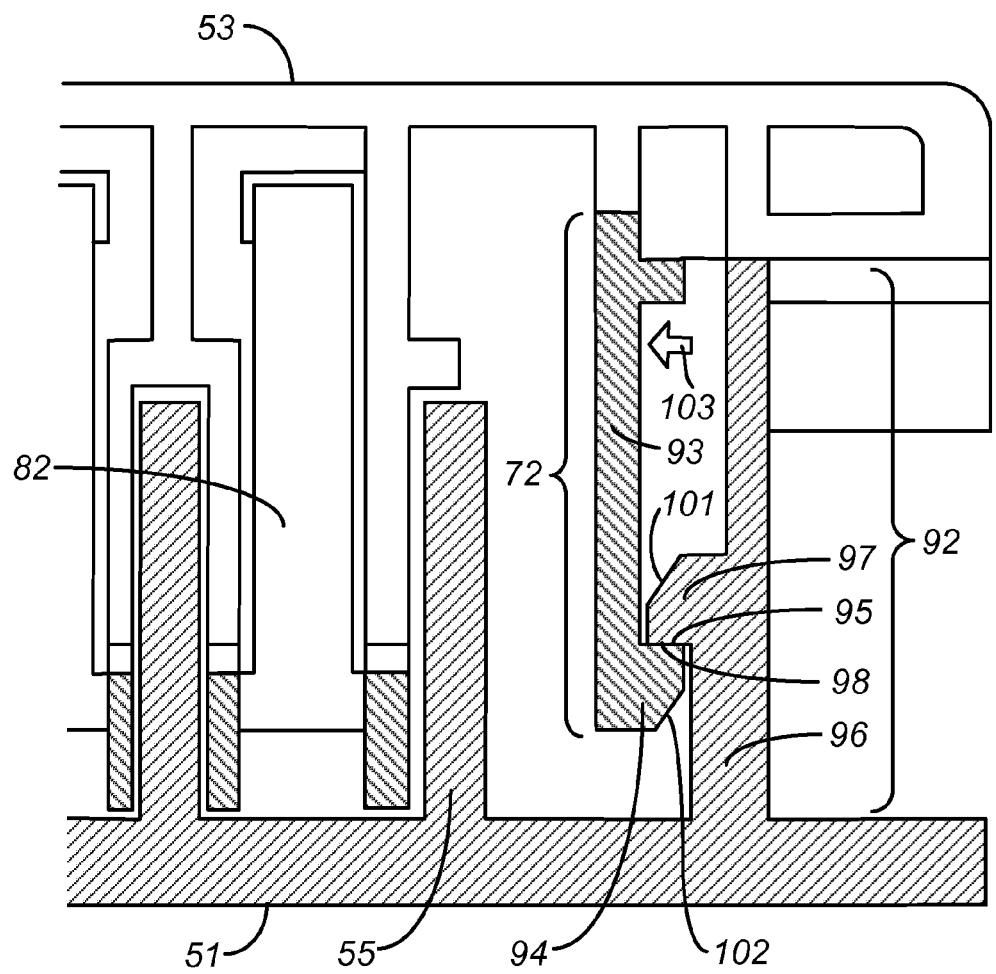
FIG. 10 is a transverse cross section of an insert and one end of the tray, both of the assembly of FIG. 6.

A third feature distinguishing the inserts in this embodiment from those of the embodiment of FIGS. 1-5 is a system of latches that secure the inserts in a fixed position on the tray. Portions 71, 72 of two of the latches are visible in the Figure. An enlarged cross section of an entire single latch is shown in FIG. 10 and discussed below.

Figure 7:
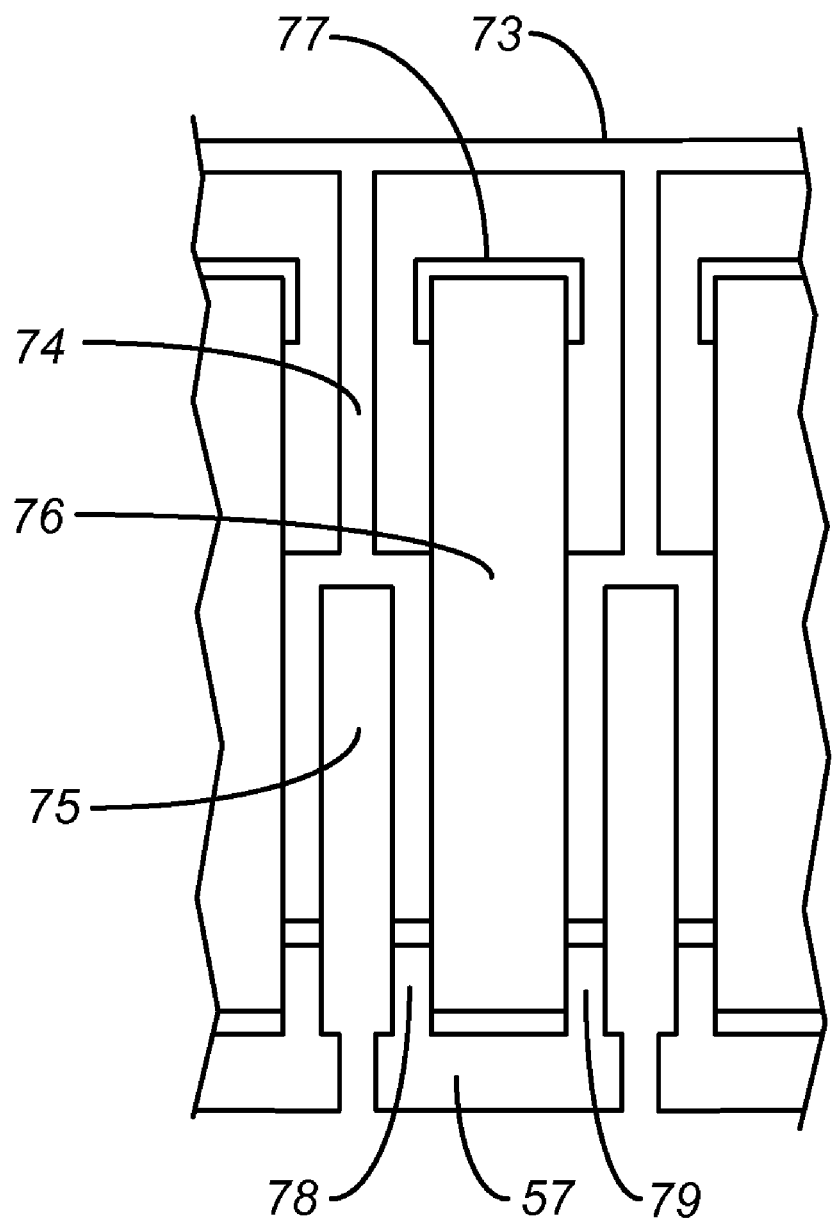
FIG. 7 is a front view of a center section of one of the inserts of the assembly of FIG. 6.

FIG. 7 shows a center section of one of the inserts 52 in a view facing the inner ends of the electrodes. The body 73 of the insert is of molded plastic or any other non-conducting and chemically inert material, and contains barriers 74 that separate the electrodes. Slots 75 in the barriers fit over the partitions 55 between the troughs in the tray (FIG. 6). The electrodes 76 are flat metal strips passing through apertures 77 in the insert body. Each electrode ends in an extended loop formed by longitudinal side arms 78, 79 that are joined at their inner ends by the crossbar 57.

Figure 8:
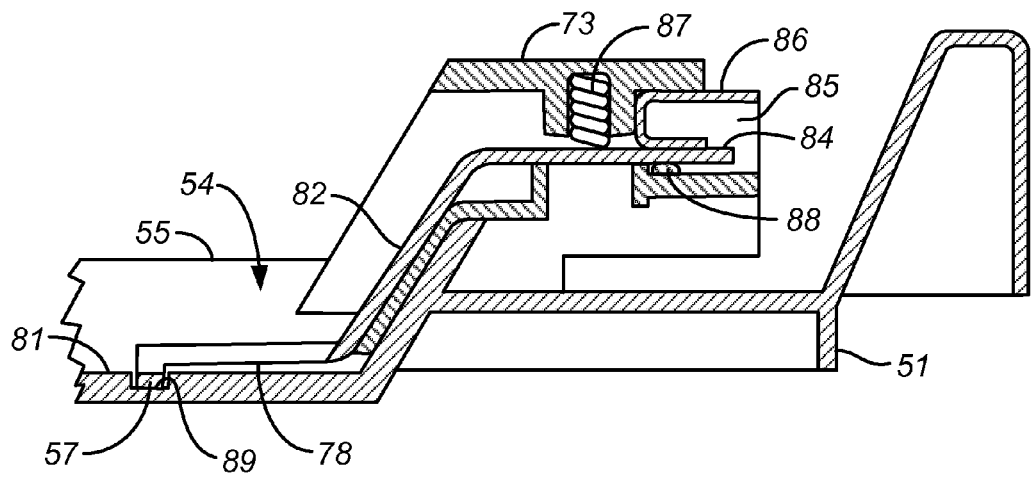
FIG. 8 is a longitudinal cross section of an insert and one end of the tray of the assembly of FIG. 6.
Figure 9:
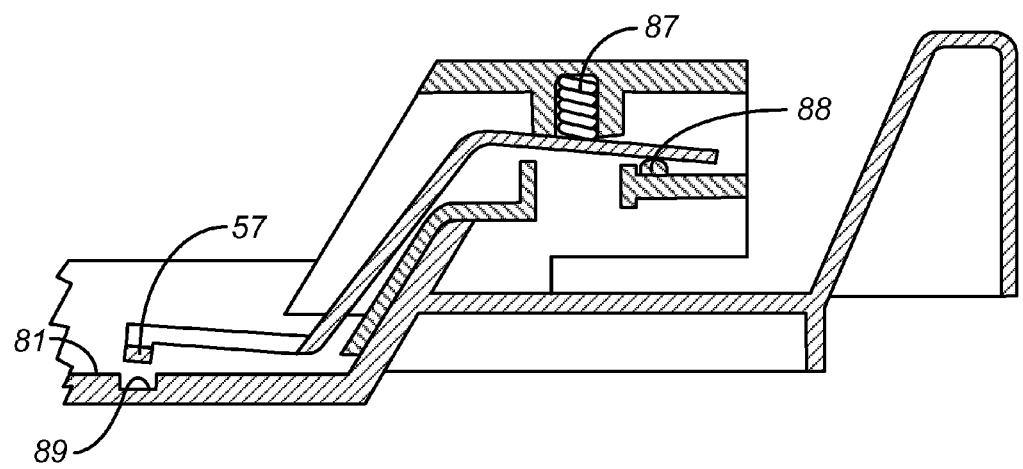
FIG. 9 is a the same longitudinal cross section as FIG. 8 with the electrode raised.

Longitudinal cross sections of one end of the tray with an insert in place are presented in FIGS. 8 and 9. Referring to FIG. 8, the cross section is cut longitudinally through a single trough 54 of the tray 51, with the floor 81 of the trough and the partition 55 separating the troughs both visible. A single electrode 82 is visible, supported by the body 73 of the insert. The inner end of the electrode is a loop formed of parallel side arms, one of which 78 is visible, terminating in the crossbar 57. The outer end of the electrode is an exposed tip 84 which extends into the interior of a hollow cavity 85 where the tip is accessible for contact with an external electric lead. As noted above, individual electrode tips can be configured as individual plugs for individual control of the voltage. Alternatively, the electrode tips on one of the inserts can be joined to a common conductive strip 86, as shown in FIG. 8. The common strip 86 can then be connected to an external lead.

The electrode 82 in this embodiment is resiliently mounted to the insert body in a manner that urges the crossbar 57 at the electrode's inner end toward the floor 81 of the trough. This is accomplished by a coil spring 87 in the insert body and a pivot point 88. The coil spring 87 urges the inner end of the electrode down, and electrode can be pressed upward against the spring by a gel strip underneath the crossbar 57. In FIG. 8, the electrode is in its lowest position, suitable for a gel strip placed above the electrode, and the crossbar 57 rests inside an indentation 89 in the floor 81 of the trough. In FIG. 9, the electrode has been pivoted around the pivot point 88 to raise the crossbar 57 above the floor 81, leaving a gap for the gel strip (not shown) which will have been placed in the trough before the insert is lowered into the tray. Since the gel strip itself pushes upward on the crossbar 57, the crossbar height is determined by the thickness of the gel strip and will adjust accordingly.

The latch system in this embodiment contains four latches, one to secure each end of each insert to one of the four corners of the tray. One of the latches is shown in FIG. 10. the latch consist of two parts, an upper part 72 (also visible in FIG. 6) near the end of the insert 53 and a lower part 92 cross section of the portion of the tray 51 that contains the of the latch. The upper part 72 includes a downwardly extending arm 93 whose lower end has a lateral projection 94 that forms a shoulder 95 while the lower part 92 is an upwardly extending wall 96 that runs parallel to the partitions 55 that separate the troughs. The upwardly extending wall 96 has a lateral protrusion 97 that forms an inverted shoulder 98 that engages the shoulder 94 on the upper portion. The two protrusions have sloping surfaces 101, 102 opposite the shoulders to allow the parts to slide together to make a snap fit. Release of the latch is achieved by finger pressure on the downwardly extending arm 93 of the upper part in the direction of the arrow 103 to disengage the shoulders.

Using either of these two constructions, i.e., that of FIGS. 1-5 and that of FIGS. 1-10, and others within the scope of the invention, isoelectric focusing can be performed on two or more samples either simultaneously or independently, and the electric potential applied across any single IPG strip can be selected independently of all other IPG strips by using differential potentials for each different pair of electrodes. The samples can be applied to the strips either before or after the strips have been placed inside the troughs.

Alternatives to the structures, shapes, and arrangements shown in the figures that are still within the concept of the present invention include the shape and configuration of the ends of the electrodes that contact the gels, the use of structural features other than slots and partitions or end walls to guide the placement of the inserts in the tray, the number of troughs in the tray, the use of inserts with fewer or more electrodes than the troughs in the tray, different latching or locking arrangements and releases, and still further variations will be readily apparent to those of skill in the art.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is not excluded from the scope of the claim. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for isoelectric focusing in a plurality of gel strips, said apparatus comprising:

a frame with a plurality of electrodes mounted thereto, each electrode terminating in an inner electrode end having upper and lower surfaces both of which comprise exposed electrode material; and a tray having a plurality of troughs, each said trough having a floor, said troughs sized and spaced to receive one gel strip per trough and one inner electrode end lying either above or below said gel strip;

wherein when said inner electrode ends are received within said troughs, said inner electrode end of each of said electrodes is variable in height between a zero height in which said inner electrode end directly contacts said floor while allowing a gel strip to rest on said upper surface and a finite height in which said lower surface is raised above said floor by a distance sufficient to receive a gel strip with said lower surface contacting an upper side of said gel strip.

2. The apparatus of claim 1, wherein said electrodes are mounted to said frame in a manner restricting all of said inner electrode ends to a uniform height above said floors.

3. The apparatus of claim 1, wherein said electrodes are mounted to said frame in a manner allowing control of the height of each inner electrode end independently of all other inner electrode ends.

4. The apparatus of claim 1, wherein said electrodes are mounted to said frame in a manner resiliently urging said inner electrode ends toward said floors.

5. The apparatus of claim 1, wherein each said electrode is pivotally mounted to said frame and said frame comprises spring means resiliently urging each said inner electrode end toward a floor of said tray.

6. The apparatus of claim 1, wherein each said trough terminates in an end wall, and said apparatus further comprises a slot in said frame sized to receive said end wall.

7. The apparatus of claim 6, wherein said slot and said end wall are configured to maintain said inner electrode ends parallel to said floors of said troughs.

8. The apparatus of claim 1, wherein said troughs are divided by partition walls, and said frame further comprises slots to receive said partition walls.

9. The apparatus of claim 1, further comprising a latch connection for joining said frame to said tray that is releasable by finger pressure.

10. The apparatus of claim 1, wherein each said electrode terminates in an electrical plug at an end of said electrode opposite said inner electrode end, with a separate electrical plug for each said electrode.

11. The apparatus of claim 1, wherein all said electrodes have outer ends opposite said inner electrode ends, and said outer ends are in electrical contact with a common electrically conductive lead mounted to said frame.

12. The apparatus of claim 1, comprising a pair of said frames, and further comprising means for joining one of said frames to each of two ends of said tray at opposing ends of said troughs.

13. The apparatus of claim 12, wherein in one frame of said pair of frames, each electrode terminates in an electrical plug at an end of said electrode opposite said inner electrode end, with a separate electrical plug for each electrode, and in the other frame of said pair of frames, all electrodes have outer ends opposite said inner electrode ends, and said outer ends are in electrical contact with a common electrically conductive lead mounted to said frame.

14. A method for performing isoelectric focusing on a plurality of samples in individual isoelectric focusing gel strips either simultaneously or independently in a single gel strip holder, said method comprising:
(a) placing said gel strips in troughs of a tray having a plurality of troughs, each trough having a floor and sized to receive one gel strip resting on said floor;
(b) either before or after step (a), applying said samples to said gel strips, with one sample per gel strip;
(c) either before, after, or between steps (a) and (b), placing a frame on said tray, said frame having a plurality of electrodes mounted thereto, each electrode terminating in an inner electrode end having parallel upper and lower surfaces both of which comprise exposed electrode material, said inner electrode ends sized and spaced to fit within said troughs with one inner electrode end per trough and both upper and lower surfaces within said trough, such that upon completion of steps (a), (b), and (c) each said gel strip is in direct contact with a single inner electrode end; and
(d) imposing an electric potential across each said strip through said contact between said strip and said inner electrode end to separate solutes in said samples along said gel strips by isoelectric focusing.

15. The method of claim 14, wherein step (c) is performed before step (a), and step (a) comprises placing said gel strips above said inner electrode ends.

16. The method of claim 14, wherein step (a) is performed after step (c), and step (c) comprises placing said inner electrode ends above said gel strips.

17. The method of claim 14, wherein said electrodes are mounted to said tray in a manner restricting all inner electrode ends to a uniform height above said floors.

18. The method of claim 14, wherein said electrodes are mounted to said tray in a manner allowing the height of each inner electrode end above the floor of the trough in which said inner electrode end is inserted to vary individually.

19. The method of claim 14, wherein said electrodes are mounted to said frame by a mounting that resiliently urges said inner electrode ends toward said floors.

20. The method of claim 14, wherein said electrodes are pivotally mounted to said frame and said frame comprises spring means resiliently urging each said inner electrode end toward a floor of said tray.

21. The method of claim 14, wherein step (c) comprises placing two said frames in said tray, one frame at each of two ends of said tray at opposing ends of said troughs, thereby placing each end of each said gel strip in direct contact with an inner electrode end on one of said frames, and step (d) comprises imposing electric potentials between inner electrode ends at opposing ends of each gel strip.

22. The method of claim 21, wherein said frames are defined as first and second frames, and each electrode of said first frame terminates in an electrical plug at an end of said electrode opposite said inner electrode end, with a separate electrical plug for each electrode of said first frame, and all electrodes of said second frame have outer ends opposite said inner electrode ends, and said outer ends are in electrical contact with a common electrically conductive lead mounted to said second frame, and wherein step (d) comprises imposing electric potentials between a inner electrode ends of said first electrodes and said common electrically conductive lead.

23. The method of claim 14, wherein each said trough terminates in an end wall, and step (a) comprises inserting said end wall in a slot in said frame.

24. The method of claim 23, wherein said slot and said end wall are configured to maintain said inner electrode ends parallel to said floors of said troughs.

25. The method of claim 14, wherein said troughs are divided by partition walls, and step (c) comprises inserting said partition walls in slots in said frame ice.

* * * * *